United States Patent [19]
Woodard et al.

[11] Patent Number: 5,525,319
[45] Date of Patent: Jun. 11, 1996

[54] BORON SILICATES, ALUMINUM SILICATES, AND PHOSPHOSILICATES FOR PURIFICATION OF DNA

[75] Inventors: Daniel L. Woodard, Raleigh; Adriann J. Howard, Durham; James A. Down, Cary, all of N.C.

[73] Assignee: Becton, Dickinson and Company, Franklin Lakes, N.J.

[21] Appl. No.: 212,095

[22] Filed: Mar. 11, 1994

Related U.S. Application Data

[63] Continuation-in-part of Ser. No. 975,744, Nov. 13, 1992, abandoned.

[51] Int. Cl.$^6$ .......................... C01B 33/113; C01B 33/26
[52] U.S. Cl. ................. 423/277; 423/304; 423/325
[58] Field of Search ................. 423/348, 277, 423/325, 328.4, 304; 106/287.1

[56] References Cited

U.S. PATENT DOCUMENTS

| | | | |
|---|---|---|---|
| 4,432,956 | 2/1984 | Zarzycki et al. | 423/338 |
| 5,075,430 | 12/1991 | Little | 536/25.41 |
| 5,155,018 | 10/1992 | Gillespie et al. | 536/23.1 |

FOREIGN PATENT DOCUMENTS

| | | |
|---|---|---|
| 0512767A1 | 11/1992 | European Pat. Off. . |
| 0555798A1 | 8/1993 | European Pat. Off. . |
| WO90/10637 | 9/1990 | WIPO . |

OTHER PUBLICATIONS

Mazurin et al. Handbook of Glass Data, Part A, Silica Glass and Binary Silicate Glasses, Physical Sciences Data 15, Elsevier, New York (1983), pp. 539, 543, and 594–595.
C. W. Chen, et al. "Recovery of DNA Segments from Agarose Gels" *Anal. Biochem.* 101, 339–341 (1980).
R. Boom, et al. "Rapid and Simple Method for Purification of Nucleic Acids" *J. Clin. Microbiol.* 28, 495–503 (1990).
B. Vogelstein, et al. "Preparative and analytical purification of DNA from agarose" *Proc. Natl. Acad. Sci.* 76, 615–619 (1979).
A. N. Murachkevich, et al. "Manufacture of Silicon Phosphate" *Chemical Abstracts* vol. 114, No. 4, Jan. 28, 1991, Abstract No. 26721h.
T. Sato, et al. "Manufacture of crystalline Laminar Sodium Borosilicate" *Chemical Abstracts* vol. 117, No. 26, Dec. 28, 1992, Abstract No. 254348j.

*Primary Examiner*—Gary L. Kunz
*Attorney, Agent, or Firm*—Donna R. Fugit

[57] ABSTRACT

Boron silicates, phosphosilicates and aluminum silicates useful as binding surfaces for DNA purification. These compounds allow DNA to be bound and eluted under native conditions (i.e., in the absence of chaotropes or alcohols) using only water, low salt buffers or physiological buffers. Methods for preparation of the compounds and methods for purifying DNA using the compounds are also provided.

8 Claims, No Drawings

BORON SILICATES, ALUMINUM SILICATES, AND PHOSPHOSILICATES FOR PURIFICATION OF DNA

This application is a continuation-in-part of U.S. Ser. No. 07/975,744 (filed Nov. 13, 1992), now abandoned.

FIELD OF THE INVENTION

The invention is in the field of molecular biology. In particular, the invention is in the area of deoxyribonucleic acid purification.

BACKGROUND OF THE INVENTION

The continued advances in molecular biology and related disciplines present continued needs for improvements in tools associated with fully appreciating and developing the advanced technology.

A wide range of technologies involve the use of deoxyribonucleic acids (DNA) in a variety of forms. For example, advances in the area of recombinant DNA technology continually require the use of DNA in the form of probes, genomic DNA, and plasmid DNA.

Advances in the area of diagnostics also continue to utilize DNA in a variety of ways. For example, DNA probes are routinely used in the detection and diagnosis of human pathogens. Likewise, DNA is used in the detection of genetic disorders. DNA is also used in the detection of food contaminants. And, DNA probes are routinely used in locating, identifying and isolating target DNA of interest for a variety of reasons ranging from genetic mapping to cloning and recombinant expression.

In many instances DNA is available in extremely small amounts, and isolation and purification procedures can be laborious and time consuming. The often time consuming and laborious procedures can lead to loss of DNA. In the purification of DNA from specimens obtained from serum, urine, and bacterial cultures, there is the added risk of contamination and false-positive results.

Typical DNA purification protocols involve the use of caustic and poisonous compositions. The typical DNA purification protocol uses high concentrations of chaotropic salts such as sodium iodide and sodium perchlorate.

There are numerous protocols for purifying DNA. As evidenced by recent activity in the area of DNA purification, there is a continued pursuit for optimal DNA purification protocols. U.S. Pat. No. 4,923,978 discloses a process for purifying DNA in which a solution of protein and DNA is passed over a hydroxylated support and the protein is bound and the DNA is eluted. U.S. Pat. 4,935,342 discloses purification of DNA by selective binding of DNA to anion exchangers and subsequent elution. U.S. Pat. No. 4,946,952 discloses DNA isolation by precipitation with water-soluble ketones. A DNA purification procedure using chaotropes and dialyzed DNA is disclosed in U.S. Pat. No. 4,900,677.

While the conventional protocols for purifying DNA are able to accomplish their goal, it is desirable to purify DNA without the use of caustic and poisonous compounds such as the most often used chaotropes and to obtain increased amounts of DNA.

SUMMARY OF THE INVENTION

The invention provides boron silicates, phosphosilicates and aluminum silicates useful as binding surfaces for purification of DNA. These compounds allow DNA to be bound and eluted under native conditions (i.e., in the absence of chaotropes or alcohols) using only water, low salt buffers or physiological buffers customarily used in procedures involving DNA. The compounds are prepared by reacting $SiCl_4$ with $BCl_3$, $AlCl_3$ or $PCl_3$ in the presence of water.

The invention can be used to purify DNA from a variety of sources and in a variety of forms. The process uses the composition of the invention and renders the use of binding buffers, such as chaotropes, optional. The DNA can be bound in aqueous solution such as TE buffer (10 mM Tris, 1 mM EDTA) at room temperature. In addition, the DNA can be eluted from the compositions of the invention in water, or generally used elution buffers such as TE or TAE. Sources of DNA for purification include bacteria, bacteriophage, specimens, plants, animals, and the like. DNA can be found in a variety of forms and includes single-stranded, double-stranded, circular, and linear. The invention can be practiced with DNA from any source in any form

DETAILED DESCRIPTION

The invention provides a composition of the formula:

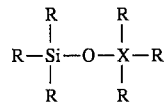

wherein X is Silicon. R may be OH, resulting in a monomer unit of the composition. Alternatively, R may be a monomer unit such that the composition comprises polymeric repeating units of the monomer. Each R may independently be either OH or a monomer unit.

The invention further provides a composition of the formula:

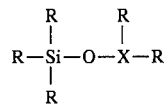

wherein X is Boron, Aluminum or Phosphorus. R may be OH, resulting in a monomer unit of the composition. Alternatively, R may be a monomer unit such that the composition comprises polymeric repeating units of the monomer. Each R may independently be either OH or a monomer unit. The repeating units described above can include from about 2 up to infinity. Ranges include about 2 to about 100,000,000 and about 2 to about 100,000.

The surface provides for binding of DNA while also allowing easy recovery of DNA from the surface. Due to the process by which the compositions are produced, the compositions of the invention may comprise mixed polymers in which X in each monomer subunit is independently either Si or one of B, P or Al. It is therefore intended that the compositions of the invention include such mixed polymers, comprising a combination of the two foregoing monomer structures.

Also provided is a process for purifying DNA which comprises contacting DNA with a composition of the formula:

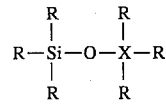

wherein X is Silicon. R may be OH, resulting in a monomer unit of the composition. Alternatively, R may be a monomer unit such that the composition comprises repeating polymeric units of the monomer. Each R may independently be either OH or a monomer unit.

The invention further provides a process for purifying DNA which comprises contacting DNA with a composition of the formula:

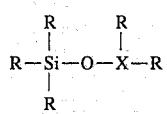

wherein X is Boron, Aluminum or Phosphorus. R may be OH, resulting in a monomer unit of the composition. Alternatively, R may be a monomer unit such that the composition comprises polymeric repeating units of the monomer. Each R may independently be either OH or a monomer unit. The repeating units described above can include from about 2 up to infinity. Ranges include about 2 to about 100,000,000 and about 2 to about 100,000.

The invention also provides a method for making the composition of the formula:

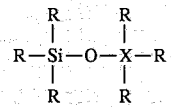

wherein X is Silicon. R may be OH, resulting in a monomer unit of the composition. Alternatively, R may be a monomer unit such that the composition comprises polymeric repeating units of the monomer. Each R may independently be either OH or a monomer unit.

The invention further provides a method for making a composition of the formula:

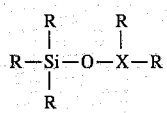

wherein X is Boron, Aluminum or Phosphorus. R may be OH, resulting in a monomer unit of the composition. Alternatively, R may be a monomer unit such that the composition comprises polymeric repeating units of the monomer. Each R may independently be either OH or a monomer unit. The repeating units described above can include from about 2 up to infinity. Ranges include about 2 to about 100,000,000 and about 2 to about 100,000.

Reaction products of a mixture of $SiCl_4$ and $BCl_3$, or $PCl_3$, or $AlCl_3$ followed by the addition of water are also provided. Generally, reaction products of water and a mixture of $SiCl_4$ and $PCl_3$, or $BCl_3$ or $AlCl_3$ result in a bead like structure comprising repeating units of the above referenced monomer units. Due to the nature of the reaction mixture, both Si and one of B, P, or Al may be present for any given X in the polymeric compositions produced. Such mixed polymers may form as each incorporated X may be derived either from $SiCl_4$ or the $BCl_3$, $PCl_3$ or $AlCl_3$ with which it is reacted.

It is possible that the electronic nature of this polymer is such that surface modifications can be made that are of a more conventional nature but are changed electronically due to the presence of this polymer being at the center of the bead (making it a more efficient surface for the purposes described in this disclosure). For example, the surface could be modified with $SiCl_4$ followed by hydration which would result in a silanol coating on the surface. The exposure of the repeating unit is what interacts with the DNA, and thus surfaces comprising the repeating unit are also suitable for practicing the invention. Surfaces which can be designed to comprise compositions of the invention include dipstick configurations, tubes, vials, filtration devices, and the like.

The procedure for obtaining the compositions of the invention generally comprises mixing $SiCl_4$ with various amounts of $PCl_3$, or $BCl_3$, or $AlCl_3$, followed by cooling. Water is then added until hydrogen chloride gas HCl(g) no longer elutes, then excess water is added to ensure complete reaction of $SiCl_4$ and $BCl_3$, or $AlCl_3$ or $PCl_3$. Amounts of reactants are generally 15:1 to 1:15.

This resulting product is stirred for about thirty (30) minutes. The resultant product is filtered then washed and dried. Suitable washing reagents include acetone and the like. The product is now ready for use in purifying DNA.

The invention also provides a process for purifying DNA which comprises contacting DNA with compositions of the invention.

The start of any DNA purification or isolation procedure requires obtaining the desired DNA from its source. Typical protocols for obtaining DNA from specimens such as serum, urine and bacterial cultures are well known and routinely carried out. Likewise, the ability to obtain DNA from genomic libraries and the like are routine. The key to the invention is the ability to purify DNA, once obtained from its source. Typical procedures for obtaining DNA end with a suspension of the DNA in solution. References include those for isolation of DNA from biological samples, Harding, J. D., Gebeyehu, G., Bebee, R., Simms, D., Ktevan, L., *Nucleic Acids Research*, 17:6947 (1989), and Marko, M. A., Chipperfield, R., and Birnboim, H. C., *Analytical Biochemistry*, 121:382 (1982). Procedures for isolation of plasmid DNA can be found in Lutze, L. H., Winegar, RA., *Nucleic Acids Research*, 20:6150 (1990). Extraction of double-stranded DNA from biological samples can be found in Yamada, O., Matsumoto, T., Nakashima, M., Hagri, S., Kamahora, T., Ueyama, H, Kishi, Y., Uemura, H., Kurimura, T., *Journal of Virological Methods* 27:203 (1990). Most DNA solutions comprise the DNA in a suitable physiological or low salt buffer such as TE (1X=10 mM Tris, 1 mM EDTA), TAE (1X=40 mm Tris-acetate, 1 mm EDTA), TBE (0.5X=45 mM Tris borate, 1 mM EDTA), or phosphate buffers (e.g., phosphate buffered saline, PBS) or in a lysate.

Once the DNA is obtained in a suitable solution, a binding matrix is typically added to the solution. Generally used binding matrixes are silica in the form of glass or diatoms. However, procedures using silica require high concentrations of chaotropes or alcohols for the DNA to bind to the surfaces. Currently used chaotropes include sodium iodide (NaI), urea, guanidinium hydrochloride, sodium perchlorate (NaClO$_4$), and potassium bromide (KBr). Chaotropes and alcohols can be toxic, caustic, flammable and/or expensive. The process of the present invention does not require the presence of chaotropes or alcohols for binding to surfaces of the invention. Processes of the invention bind DNA in an aqueous solution at room temperature and elute the DNA in water at 37° C. Suitable aqueous solutions include the physiological buffers and low salt buffers typically used with DNA (e.g., TE, TAE, TBE, phosphate buffers, etc.), or water. However, if desired, chaotropes, alcohols and the like can be used with the process of the invention.

Typical procedures for using the process of the invention include the addition of the composition of the invention to a solution of DNA in water or a low salt or physiological buffer. This may be followed by the addition of a binding buffer, i.e., a buffer which contains chaotropes or alcohol. At this point, it is advantageous that the process of the invention does not require addition of a binding buffer, as DNA will bind to the compositions of the invention in the absence of such binding buffers. The solution can be incubated for a brief period at room temperature. After spinning, the supernatant can be discarded and the pellet washed. The DNA can then be eluted, for example by heating in water, or using low salt or physiological buffers.

The composition of the invention is typically used in weight ranges from about 1:10 to 1:1 composition weight:water in the DNA-containing solution. Preferably excess amounts of water are avoided. Low salt and physiological buffers such as those described above can be used in place of water in the DNA solution.

Next, a binding buffer, if used, is added to the mixture of DNA-containing solution and inventive composition. After a brief incubation period at room temperature, although a range of about 20° C. to about 40° C. is acceptable, from about 1 to about 20 minutes, preferably about 10 minutes, the container can be spun to obtain pellet and supernatant fractions. The supernatant is separated and the pellet is washed with a reagent such as ethanol diluted with 50 mM Tris. A preferred wash reagent concentration is 80% ethanol. DNA can then be eluted from the compositions of the invention by using low salt and physiological elution buffers such as TE buffer, 1X TAE buffer, and 1X TBE buffer. More importantly, the use of elution buffers can be eliminated altogether, and the DNA eluted in water by heating. For maximum yields the elution step can be repeated.

The chemical compositions of the invention may be conveniently assembled into a kit. A kit comprising the composition of the invention may include the composition in a container, such as a vial, with a suitable buffer, such as TE buffer or TAE buffer and may optionally include a container of a chaotrope or alcohol binding buffer, a container of wash buffer (e.g., a solution of ethanol diluted with 50 mM tris or 1X TAE), and a container of elution buffer, such as TE buffer, 1X TAE buffer, or 1X TBE buffer). Such a kit would allow convenient purification of DNA.

The following examples illustrate the specific embodiments of the invention described in this document. As would be apparent to skilled artisans, various changes and modifications are possible and are contemplated within the scope of the invention described.

EXAMPLE 1

The purpose of this experiment is to synthesize 10 boron silicate polymers. The polymers contain various amounts of boron because incorporation of boron, a less electropositive atom than silicon, into the polymer will change the electronic nature of the surface and may effect its ability to purify DNA from an aqueous sample by solid phase extraction.

Materials $BCl_3$ in $CH_2Cl_2$(1M) (Aldrich, Milwaukee, Wis.)
$SiCl_4$ (Petrarch systems, Bristol, Pa.)

Procedure: Ten experiments were set up the same way except the percentage of $BCl_3$ was varied as shown below.

| Surface | $BCl_3$ | | $SiCl_4$ | |
|---|---|---|---|---|
| | µL | mMol | g | mMol |
| 1 | 1.0 | 1.0 | 1.70 | 10.0 |
| 2 | 2.0 | 2.0 | 1.70 | 10.0 |
| 3 | 5.0 | 5.0 | 1.70 | 10.0 |
| 4 | 7.0 | 7.0 | 1.70 | 10.0 |
| 5 | 10.0 | 10.0 | 1.70 | 10.0 |
| | | | µL | mMol |
| 6 | 5.0 | 5.0 | 123.0 | 1.0 |
| 7 | 5.0 | 5.0 | 247.0 | 2.0 |
| 8 | 5.0 | 5.0 | 370.0 | 3.0 |
| 9 | 5.0 | 5.0 | 493.0 | 4.0 |
| 10 | 5.0 | 5.0 | 0.0 | 0.0 |

The $SiCl_4$ and $BCl_3$ are mixed and cooled to about 5° C. for 20 minutes. With stirring, $H_2O$ is slowly added until HCl(g) no longer elutes. 5 mL excess $H_2O$ is added to ensure complete reaction. Stirred 1 hour.

Filter, wash 3X10 mL $H_2O$ then 3X10 mL acetone, air dry 25 minutes and heat dry 1 hour.

EXAMPLE 2

Phosphorus has approximately the same electronegativity as Boron. Boronsilicates have been shown to work very well for DNA purification. Therefore, if polarization of the surface is important in DNA adhesion/elution then Phosphosilicates should work as well as boronsilicates for DNA purification.

Materials:

$SiCl_4$ (Petrarch Systems)
$PCl_3$ - 2M in $CH_2Cl_2$ (Aldrich)

Ten experiments were done exactly the same way except that the amount of $PCl_3$ was different in each experiment. The following table describes each of the ten experiments.

| Experiment | $SiCl_4$ | | $PCl_3$ | | |
|---|---|---|---|---|---|
| | mL | mMol | cg | mL | mMol |
| 1 | 1.340 | 10.0 | 0.1 | 0.5 | 1.0 |
| 2 | 1.340 | 10.0 | 0.3 | 1.5 | 3.0 |
| 3 | 1.340 | 10.0 | 0.5 | 2.5 | 5.0 |
| 4 | 1.340 | 10.0 | 0.7 | 3.5 | 7.0 |
| 5 | 1.340 | 10.0 | 1.0 | 5.0 | 10.0 |
| 6 | 0.65 | 5.0 | 1.5 | 3.75 | 7.5 |
| 7 | 0.65 | 5.0 | 2.0 | 5.0 | 10.0 |
| 8 | 0.65 | 5.0 | 3.0 | 7.5 | 15.0 |
| 9 | 0.65 | 5.0 | 4.0 | 10.0 | 20.0 |
| 10 | 0.65 | 5.0 | 5.0 | 12.5 | 25.0 |

In the typical experiment, the $SiCl_4$ is added to a 25 mL erlenmeyer flask and cooled to 0° C. in an ice bath for about 10 minutes. The $PCl_3$ is then added and cooled for 5 minutes. $H_2O$ was added very slowly, about 2 drops per minute, until white gas no longer eluted. Stir 5 minutes and add 3 mL in 1 mL increments. Stir at room temperature for 15 minutes. Filter, wash the solid with 3X10 mL $H_2O$ then 3*10 mL acetone. Air dry 15 minutes, heat dry one (1) hour. Store in a dessicator.

EXAMPLE 3

The purpose of the following experiment is to synthesize aluminum silicate polymers containing various amounts of aluminum. Aluminum is more electropositive than silicon and, therefore, as the amount of aluminum in the polymer increases so should the amount of DNA adhering to that polymer.

Starting Materials

AlCl$_3$, 1M in nitrobenzene (Aldrich)

SiCl$_4$ (Petrarch System)

Procedure

Eight experiments were performed the same way except that the amount of AlCl$_3$ was varied from one to the next.

| Experiment | SiCl$_4$ | | AlCl$_3$ | |
|---|---|---|---|---|
| | mL | mMol | mL | mMol |
| 1 | 1.34 | 10.0 | 1.0 | 1.0 |
| 2 | 1.34 | 10.0 | 3.0 | 3.0 |
| 3 | 1.34 | 10.0 | 5.0 | 5.0 |
| 4 | 1.34 | 10.0 | 7.0 | 7.0 |
| 5 | 1.34 | 10.0 | 10.0 | 10.0 |
| 6 | 0.67 | 5.0 | 7.5 | 7.5 |
| 7 | 0.67 | 5.0 | 10.0 | 10.0 |
| 8 | 0.67 | 5.0 | 15.0 | 15.0 |

In a typical experiment the AlCl$_3$ and SiCl$_4$ are mixed together and cooled in an ice bath for 15 minutes. Water is added dropwise, with vigorous stirring. Very slowly (5 drops every 2 minutes), water is added until no HCl(g) elutes from the reaction vessel.

Add about 3 mL H$_2$O to ensure complete reaction. Stir at room temperature for 15 minutes.

Filter, wash 3X10 mL acetone, 3X20 mL H$_2$O, 3X10 mL acetone. Air dry for 20 minutes, heat dry one (1) hour. Store in a dessicator.

EXAMPLE 4

This experiment describes how the DNA binding capacity of SUPER FINE SUPER FLOSS CELITE (the industry standard, Manville) was determined and what that capacity is. It was determined that SUPER FINE SUPER FLOSS CELITE strongly binds and elutes DNA at 2.5M with NaClO$_4$ as the binding buffer.

Materials:

Super Fine Super Floss (SFSF) (Sample from Manville, Denver, Colo. (1:5 w/w in H$_2$O))

λDNA (BRL Cat. 56125A)

50 mM Tris pH7.0 (Dilute from 1M stock) BRL Cat. 5505UA

PREP-A-GENE KIT (Bio-Rad, Richmond, Calif.)

Binding Buffers (Diluted from 6M stock) NaClO$_4$ Fisher Cat. 5490–500

Wash Buffer 80% Ethanol in 50 mM Tris, pH7.0

Elution Buffer

Milli Q H$_2$O

Ethidium Bromide (10 mg/ml) Sigma Cat. E-8751

1% agarose BRL Cat. 5510UA

1X TAE (from 50X stock) Tris Base-Sigma CAT T-1503

Acetic Acid - Fisher A38-500

EDTA - Sigma CAT ED2550

Type II Loading Dye (25% Ficoll 400, 0.25% Bromophenol Blue, 0.25% xylene cyanol Ficoll 400 - Sigma CAT F4375, Bromophenol Blue - BIO-RAD CAT 161-0404

Xylene Cyanole - Sigma CAT X-4126

Type 57 and 55 POLAROID Film

METHODS

1. Two groups of reactions are set up, one for each surface type. Each surface has 8 tubes containing 50 µl of the DNA solution. This solution is 0.5 µl λDNA in 50 µl of 50 mM Tris, pH7.0 for 31 µg DNA/reaction. The titration ranges from 0M NaClO$_4$ to 6M NaClO$_4$.

2. Add 20 µl of each surface to the reaction mixes.

3. Add 400 µl Binding Buffer according to the titration. For Prep-A-Gene this was 0.0M, 2.0M, 2.5M, 3.0M, 3.5M, 4.0M, 4.5M, and 6.0M NaClO$_4$. For SFSF, the titration is 0M, 1.0M, 1.5M, 2.0M, 2.5M, 3.0M, 3.5M, and 4.0M NaClO$_4$.

4. Incubate for 10 minutes, with rocking, at room temperature.

5. Spin and discard supernatant.

6. Wash pellet 2 times with 80% ethanol/50 mM Tris, pH7.0.

7. Elute DNA in 20 µl H$_2$O 37° C., 10 minutes.

8. Spin and remove supernatant to a separate tube. Repeat elution step and combine supernatants for 40 µl total.

9. Add 2 µl, Type II loading dye to each tube.

10. Load onto a 1% agarose, 1X TAE gel. Run for 25 minutes at 100–130 volts in 1 X TAE buffer.

11. Stain with ethidium bromide in H$_2$O (~1:1000) for ~15 minutes. Destain for ~20– 30 minutes.

12. Photograph over UV light with Type 57 Polaroid film. If possible, take negatives with Type 55 film.

Results and Conclusions

Prep-A-Gene shows no elution of DNA until 3.0M NaClO$_4$, whereas SFSF binds DNA in its native state and elutes strongly at 2.5M NAClO$_4$. Clearly SFSF performs better than Prep-A-Gene.

EXAMPLE 5

This experiment describes the DNA binding capacity of boron silicates, phosphosilicates, and aluminum silicates.

Electrophoresis shows that many of these surfaces give good recovery of DNA down to 1M NaClO$_4$ as the binding buffer, when a binding buffer is used. This is superior to the Super Fine Super Floss Celite which gives good recovery only down to 2.5M NaCl$_4$ as the binding buffer. It would also appear from gel electrophoresis analysis that some of these surfaces give equal or greater recovery of DNA under native conditions (0M binding buffer, i.e., in the absence of chaotrope. See Methods, step 3, of example 4) as they do at these lower levels of NaClO$_4$.

Materials

Compositions of the invention prepared in substantial accordance with examples 1, 2, and 3 (boron silicates, phosphosilicates and aluminum silicates).

SUPER FINE SUPER FLOSS (Manville) 1:5 weight:water

Methods

Eight reaction groups are tested for each surface shown below. The binding buffer concentrations, when a binding buffer is used, are 1.0M, 1.5M, 2.0M, 2.5M, 3.0M, 3.5M, 4.0M with SFSF at 3.0M NaClO$_4$ as the standard. See Example 4 for procedure.

Results

TABLE I

| Surface | Results of DNA Binding Studies: | | |
|---|---|---|---|
| | Molar Percentage of Boron, Aluminum or Phosphorous compound in the reaction | DNA Binding 1M-4M [NaClO$_4$] | Binding in water |
| 1 | 9.1 | ++ 1.5M | |
| 2 | 16.6 | – | |
| 3 | 33.5 | +++ | Yes |
| 4 | 42.2 | ++ 1.5M | |
| 5 | 50.0 | – | |
| 6 | 55.6 | +++ | Yes |
| 7 | 62.5 | ++ 1.5M | |
| 8 | 71.4 | ++ 2.0M | |
| 9 | 83.3 | +++ | Yes |
| 10 | 9.1 | – | |
| 11 | 16.6 | ++ 1.5M | |
| 12 | 33.3 | ++ 1.5M | |
| 13 | 42.2 | + | |
| 14 | 50.0 | +++ | Yes |
| 15 | 62.5 | +++ | Yes |
| 16 | 66.6 | ++ | |
| 17 | 75.0 | +++ | Yes |
| 18 | 80.0 | +++ | Yes |
| 19 | 83.3 | +++ | Yes |
| 20 | 9.1 | +++ | Yes |
| 21 | 23.1 | + | |
| 22 | 33.3 | + | |
| 23 | 41.2 | – | |
| 24 | 50.0 | – | |
| 25 | 60.8 | – | |
| 26 | 66.6 | – | |
| 27 | 75.0 | – | |

– If DNA binding occurred, the DNA didn't elute off.
+ Trace amounts of DNA elute across the titration.
++ Near complete elution down to the indicated molarity of binding buffer.
+++ Strong elution of DNA across the titration.
+, + and +++ were determined by visualization of ethidium bromide stained gels.
1–9 boron silicates
10–19 phosphosilicates
20–27 aluminum silicates Conclusion:

Several surfaces out-perform SFSF Celite both in the amount of DNA recovered from solution and the concentration of binding buffer required to bring about this recovery. According to agarose gel electrophorsis analysis, nearly 100% recovery of DNA from solution with as little as to 1.0M NaClO$_4$ as the binding buffer were achieved with several of the surfaces. Other surfaces according to the invention gave nearly 100% recovery of DNA after binding in water, i.e., eliminating the need for chaotrope in the binding buffer.

Although the invention has been described with respect to specific modifications, the details thereof are not to be construed as limitations, for it will be apparent that various equivalents change and modifications may be resorted to without departing from the spirit and scope thereof, and it is understood that such equivalent embodiments are to be included therein.

What is claimed is:

1. A DNA binding compound produced by a process comprising the steps of:
    a) preparing a reaction mixture consisting essentially of SiCl$_4$ and a second component selected from the group consisting of:
        a molar percentage of BCl$_3$ of about 33.5%;
        a molar percentage of BCl$_3$ of about 55.6%;
        a molar percentage of BCl$_3$ of about 83.3%;
        a molar percentage of PCl$_3$ of about 50.0%–83.3%; and
        a molar percentage of AlCl$_3$ of about 9.1%;
    b) cooling the reaction mixture;
    c) adding water to the reaction mixture until elution of gas is complete, and;
    d) recovering the compound.

2. The compound of claim 1 which is produced by reacting a mixture of SiCl$_4$ and BCl$_3$ with water.

3. The compound of claim 1 which is produced by reacting a mixture of SiCl$_4$ and AlCl$_3$ with water.

4. The compound of claim 1 which is produced by reacting a mixture of SiCl$_4$ and PCl$_3$ with water.

5. The compound of claim 1 the reaction mixture is cooled at about 0°–5° C. for about 10–20 minutes and reacted with the water for about 15 minutes to 1 hour after elution of gas is complete.

6. A kit for purifying DNA which comprises:
    a) a DNA binding compound produced by a process comprising the steps of:
        i) preparing a reaction mixture consisting essentially of SiCl$_4$ and a second component selected from the group consisting of:
            a molar percentage of BCl$_3$ of about 33.5%;
            a molar percentage of BCl$_3$ of about 55.6%;
            a molar percentage of BCl$_3$ of about 83.3%;
            a molar percentage of PCl$_3$ of about 50.0%–83.3%; and
            a molar percentage of AlCl$_3$ of about 9.1%;
        ii) cooling the reaction mixture;
        iii) adding water to the reaction mixture until elution of gas is complete, and;
        iv) recovering the compound; and;
    b) at least one of the following reagents:
        i) a binding solution selected from the group consisting of water, low salt buffers and physiological buffers;
        ii) an ethanol washing solution, and;
        iii) an elution solution selected from the group consisting of water, low salt buffers and physiological buffers.

7. The kit of claim 6 comprising the DNA binding compound in a buffer.

8. The kit of claim 7 comprising an elution solution selected from the group consisting of TE buffer, TAE buffer and TBE buffer.

* * * * *